(12) United States Patent
Satyawali et al.

(10) Patent No.: US 10,730,022 B2
(45) Date of Patent: Aug. 4, 2020

(54) PROCESS FOR THE SEPARATION OF ORGANIC COMPOUNDS

(71) Applicant: VITO NV, Mol (BE)

(72) Inventors: Yamini Satyawali, Mol (BE); Dominic Ormerod, Mol (BE); Karolien Vanbroekhoven, Mol (BE); Anita Buekenhoudt, Mol (BE)

(73) Assignee: VITO NV, Mol (BE)

( * ) Notice: Subject to any disclaimer, the term of this patent is extended or adjusted under 35 U.S.C. 154(b) by 34 days.

(21) Appl. No.: 16/062,615

(22) PCT Filed: Dec. 16, 2016

(86) PCT No.: PCT/EP2016/081516
§ 371 (c)(1),
(2) Date: Jun. 14, 2018

(87) PCT Pub. No.: WO2017/103163
PCT Pub. Date: Jun. 22, 2017

(65) Prior Publication Data
US 2018/0369759 A1 Dec. 27, 2018

(30) Foreign Application Priority Data

Dec. 17, 2015 (EP) ..................................... 15200937

(51) Int. Cl.
*B01D 69/02* (2006.01)
*B01D 69/14* (2006.01)
(Continued)

(52) U.S. Cl.
CPC ......... *B01D 69/144* (2013.01); *B01D 61/246* (2013.01); *B01D 69/02* (2013.01);
(Continued)

(58) Field of Classification Search
None
See application file for complete search history.

(56) References Cited

U.S. PATENT DOCUMENTS

| 4,961,881 A * | 10/1990 | Ou | C07C 67/56 554/193 |
| 6,281,003 B1 * | 8/2001 | Hirrlinger | C12P 13/02 435/280 |

(Continued)

FOREIGN PATENT DOCUMENTS

| WO | WO 01/09042 A1 | 2/2001 | |
| WO | WO-2010106167 A1 * | 9/2010 | B01D 67/0093 |

OTHER PUBLICATIONS

Börner, et al., "A process concept for high-purity production of amines by transaminase-catalyzed asymmetric synthesis: Combining enzyme cascade and membrane-assisted ISPR," Org. Process Res. Dev., 2015, 19, 7, 793-799 (https://doi.org/10.1021/acs.oprd.5b00055) (Year: 2015).*

(Continued)

*Primary Examiner* — Chester T Barry
(74) *Attorney, Agent, or Firm* — Knobbe, Martens, Olson & Bear LLP

(57) ABSTRACT

A membrane based process separates amines or organic acids from a solution containing at least one amine or at least one organic acid according to their hydrophobic properties. The more hydrophobic amine or organic acid passes the hydrophobic membrane into an acidic aqueous solution, thus selectively removing the amine or organic acid from the first solution. The process is particularly suitable to obtain chiral amines in high yield. A transaminase-catalyzed transamination of an amino donor and amino acceptor is combined with a hydrophobic membrane separation of the produced chiral amine. The selective removal of the chiral amine from the (Continued)

reaction mixture promotes the further transformation of the amino acceptor into the product chiral amine.

16 Claims, 3 Drawing Sheets

(51) Int. Cl.
    *B01D 61/24*     (2006.01)
    *B01D 71/02*     (2006.01)
    *C12P 13/00*     (2006.01)
    *C07C 209/86*     (2006.01)
    *C12P 7/28*     (2006.01)

(52) U.S. Cl.
    CPC ............ *B01D 71/02* (2013.01); *C07C 209/86* (2013.01); *C12P 7/28* (2013.01); *C12P 13/001* (2013.01); *B01D 2257/70* (2013.01); *B01D 2323/04* (2013.01); *B01D 2323/36* (2013.01); *B01D 2325/38* (2013.01)

(56) References Cited

U.S. PATENT DOCUMENTS

| | | | |
|---|---|---|---|
| 6,716,352 B1* | 4/2004 | Livingston | B01D 61/246 210/490 |
| 8,802,880 B1* | 8/2014 | Adam | C11B 7/0008 554/191 |
| 2015/0053611 A1* | 2/2015 | Wang | B01D 71/64 210/500.23 |

OTHER PUBLICATIONS

Andrade et al., Continuous Flow Synthesis of Chiral Amines in Organic Solvents: Immobilization of *E. coli* Cells Containing Both w Transaminase and PLP, Org. Lett. 2014, 16, 23, 6092-6095 (https://doi.org/10.1021/ol502712v) (Year: 2014).*

Andrade, L.H., et al., Continuous Flow Synthesis of Chiral Amines in Organic Solvents: Immobilization of *E. coli* Cells Containing Both Omega-Transaminase and PLP, Organic Letters 16(23):6092-6095, Dec. 5, 2014.

Borner, T., et al., A Process Concept for High-Purity Production of Amines by Transaminase-Catalyzed Asymmetric Synthesis: Combining Enzyme Cascade and Membrane-Assisted ISPR, Organic Process Research and Development 19(7):793-799, Jul. 17, 2015.

Shin, J.S., et al., Kinetic Resolution of Chiral Amines With Omega-Transaminase Using an Enzyme-Membrane Reactor, Biotechnology and Bioengineering 73(3):179-187, May 5, 2001.

Office Action issued in IL patent application No. 260047, dated Feb. 5, 2020.

Office Action issued in IN patent application No. 201837022883, dated Mar. 17, 2020.

* cited by examiner

SUBSTRATE

PRODUCT

PROCESS FOR THE SEPARATION OF ORGANIC COMPOUNDS

FIELD OF THE INVENTION

The present invention relates to improved methods for the membrane based separation of organic compounds, particularly hydrophobic organic acids and amines. More in particular, the present invention relates to improved methods for the membrane based separation of amines, such as chiral amines.

BACKGROUND TO THE INVENTION

In general, amines are organic compounds comprising a functional group that contains a basic nitrogen atom with a lone pair, which can bind a proton to form an ammonium ion. Amines and, particularly chiral amines, are ubiquitous in biology and industry. Amines, particularly chiral amines, are key building blocks in many pharmaceutical, agrochemical and chemical applications. Chiral amines are particularly important in the production of physiologically active compounds. Moreover, in many applications of chiral amines, only one particular optically active form, either the (R) or the (S) enantiomer has the desired physiological activity.

(Chiral) amines can be produced both by chemical and biocatalytic synthesis routes. Chemical synthesis of optically active chiral amines via a one-step procedure requires high chemo-, regio-, diastereo-, and enantiocontrol. One of the biocatalytic synthesis routes to obtain chiral amines uses the enzyme transaminase (EC 2.6.1.X; also known as aminotransferases). Transaminases are pyridoxal phosphate dependent enzymes and catalyze the transfer of an amine ($-NH_2$) group from an amine donor, for instance an amino acid or a simple amine such as 2-propylamine, to a pro-chiral acceptor ketone, yielding a chiral amine as well as a co-product ketone or alpha-keto acid, in the presence of the cofactor pyridoxal phosphate (PLP) which is continuously regenerated during the reaction (FIG. 1). Transaminases, particularly (R)- and (S)-selective transaminases, have received much attention as suitable catalysts for producing chiral amines, as they allow the direct asymmetric synthesis of (optically active) chiral amines from pro-chiral ketones.

Although the transaminase catalysed synthesis of chiral amines presents a high enantio- and regioselectivity, the transamination reaction is a reversible reaction, often with an unfavourable thermodynamic equilibrium which limits obtaining high chiral amine yields. Accordingly, an amine mixture is obtained comprising the chiral amine and the amine donor, requiring further purification of the chiral amine. In addition, the transaminase catalysed chiral amine synthesis is prone to substrate and product inhibition. In addition, substrate solubility issues may hinder the reaction as well.

Börner et al. (Organic Process Research & Development, 2015, 19(7), 793-799) describes an enzymatic chiral amine synthesis process setup combined with a selective solvent extraction of the product chiral amine, comprising a so-called reaction phase and a so-called stripping phase at different pH, separated by a supported liquid membrane, in casu a membrane with the pores loaded/impregnated with undecane. In the reaction phase (at pH≥9), the transaminase reaction takes place with isopropyl amine (IPA) or alanine (ALA) as amine donor. Although all uncharged substrate and product compounds can be (selectively) extracted by the organic solvent of the liquid membrane and can pass through the liquid membrane to the stripping phase (at pH<3), back extraction from the stripping phase into the organic membrane phase is prevented for the charged compounds (in casu the non-aminoacid amine donor and amine product in the stripping phase). This setup results in a selective in situ product removal, which steers the reaction equilibrium towards chiral amine synthesis. However, the liquid-membrane setup used in this study is not stable due to the liquid in the membrane pores being prone to leaking out during operation, requiring regularly regeneration of the liquid membrane, and is sensitive to transmembrane pressure differences. This setup is thus less suitable for long-term, large scale chiral amine synthesis and separation.

WO01/09042 discloses a process for recovering an aromatic amine dissolved in an aqueous fluid comprising transferring the undissociated aromatic amine from the aqueous fluid to an acidic stripping solution across a membrane, wherein the membrane is a non-porous, elastomeric (polymeric) selectively permeable membrane. In the process of WO01/09042, the uncharged/undissociated aromatic amines pass through the membrane by diffusion to the acidic stripping phase, which can be considered as the dissolution of the undissociated aromatic amines within the polymeric membrane. Similar as in Börner et al (Organic Process Research & Development, 2015, 19(7), 793-799), back extraction from the acidic stripping phase is prevented for the charged compounds. However, the performance and stability of an elastomeric polymeric membrane of WO01/09042 is often negatively affected when using particular solutions or liquids in the separation process or during membrane cleaning.

There remains a need in the art for the improved separation of organic compounds such as amines or organic acids from a solution, particularly from a solution comprising a chiral amine and/or multiple amines, that overcomes the limitations of the prior art. In this context, there is a particular need for improved enzymatic processes and systems to produce chiral amines that overcome at least some of the above indicated limitations of the transamination reaction and at the same time allow for long term application, which can be adapted to specific substrate donor amines/ketones and/or product amines.

SUMMARY OF THE INVENTION

The inventors have developed an efficient and stable membrane based separation process suitable for the separation of organic amine or acid compounds. Advantageously, the more hydrophobic amine or organic acid can be selectively separated or recovered from a mixture of at least two amines or organic acids, which differ in hydrophobicity, even if they have similar pKa values. Indeed, in particular embodiments, the more hydrophobic amine or organic acid can be selectively extracted across a porous inorganic hydrophobic membrane, despite the presence of pores, while the less hydrophobic amine(s) or organic acid(s) are retained by said porous inorganic hydrophobic membrane. Advantageously, an inorganic or ceramic membrane is chemically inert and exhibits high mechanical, thermal and hydrothermal stabilities, favoring a long term use of the separation processes and chiral amine production processes envisaged herein.

While this system has broad applicability, it is of particular interest for the separation of an amine from a solution comprising at least one amine, particularly for the separation of a chiral amine. Moreover, this separation method is particularly useful in an improved transaminase catalysed chiral amine production method as envisaged herein, wherein the transaminase catalysed reaction between a donor amine and acceptor ketone is combined with a hydrophobic membrane based separation of the produced chiral amine. Advantageously, the selective removal of the produced chiral amine across the membrane as envisaged herein, while at the same time the donor amine is retained and thus remains available for reaction, promotes the transaminase reaction.

Accordingly, in particular embodiments a method for the separation of an amine or organic acid from a first solution comprising at least one amine or organic acid, respectively, is provided, said method comprising
(i) contacting said first solution comprising at least one amine or organic acid with a non-liquid hydrophobic membrane; and
(ii) extracting an amine or organic acid from said first solution comprising at least one amine or organic acid, respectively, into a second solution across said hydrophobic membrane, wherein said hydrophobic membrane separates said first solution and said second solution.

In particular embodiments, said hydrophobic membrane is a porous hydrophobic inorganic membrane, i.e. a hydrophobic inorganic membrane containing pores and voids, preferably, a porous, hydrophobic, inorganic membrane functionalized with an organic functional group. Preferred pore sizes range from 0.5 nm to about 100 or 200 nm, more preferably from about 0.5 to about 30, 40 or 50 nm, even more preferably from about 0.5 or 1 nm to about 5, 10 or 20 nm, such as from 0.5 nm to 10 nm, as measured by permporometry or nitrogen sorption techniques as known by the skilled person in the art. In particular embodiments, said inorganic membrane comprises an oxide or hydroxide of an element M1 and said organic functional group is linked to said inorganic membrane via a M1-carbon bond, a M1-O—P-carbon bond or a M1-O—Si-carbon bond. Preferably, said organic functional group is selected from the group consisting of (a) haloalkyl, preferably fluoroalkyl or perfluoroalkyl, more preferably fluoro$C_1$-$C_{16}$alkyl or perfluoro$C_1$-$C_{16}$alkyl, more preferably fluoro$C_1$-$C_8$alkyl or (per)fluoro$C_1$-$C_8$alkyl; (b) aryl, preferably $C_6$-$C_{16}$aryl, more preferably $C_6$-$C_{10}$aryl; and (c) haloaryl, preferably fluoroaryl or perfluoroaryl, more preferably fluoro$C_6$-$C_{16}$aryl or perfluoro$C_6$-$C_{16}$aryl, more preferably fluoro$C_6$-$C_{10}$aryl or perfluoro$C_6$-$C_{10}$aryl.

In particular embodiments, said first solution is an aqueous alkaline solution comprising at least one amine. In other particular embodiments, said first solution is an organic solvent solution comprising at least one amine.

In particular embodiments, the pH value of said second solution is configured to avoid the back extraction across said hydrophobic membrane as described herein of said amine or organic acid, respectively. In particular embodiments, said method is a method for the separation of an amine and said second solution is an acidic aqueous solution. In other particular embodiments, said method is a method for the separation of an organic acid and said second solution is an alkaline aqueous solution.

In particular embodiments, said amine in said first solution comprising an amine is a chiral amine. In preferred embodiments, said method for the separation of an amine further comprises the step of forming a chiral amine by contacting an amino donor and a prochiral amino acceptor with a transaminase, thus obtaining a chiral amine in said first solution, prior to step (i) and (ii). Accordingly, said first solution may comprise an amino donor and a prochiral amino acceptor, which is subsequently contacted with a transaminase. Preferably, in said transaminase reaction, the amino donor is 2-propyl amine.

In particular embodiments, said method further comprises the step of recovery of the amine from the acidic second solution, or the recovery of an organic acid from an alkaline second solution.

In particular embodiments, said method is performed using a membrane contactor setup, wherein the first solution is fed to a first compartment of a membrane contactor module and wherein step (ii) transfers said amine or organic acid to a second compartment of the membrane contactor module, comprising said second solution.

BRIEF DESCRIPTION OF THE DRAWINGS

The following description of the figures of specific embodiments is merely exemplary in nature and is not intended to limit the present teachings, their application or uses.

DETAILED DESCRIPTION OF INVENTION

Figure 1:
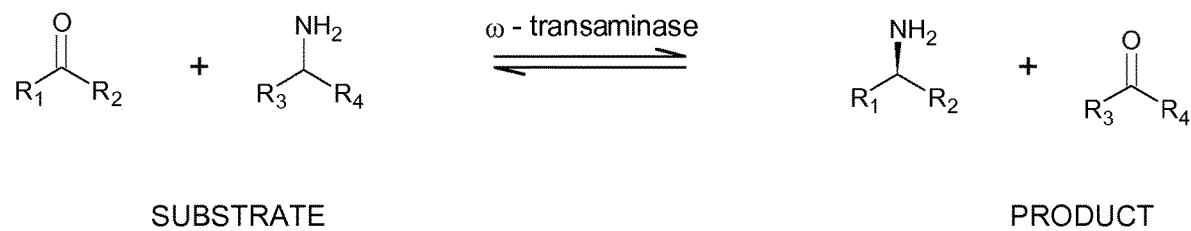
FIG. 1 schematically represents the transaminase catalysed transamination reaction, whereby an amino acceptor (i.e. a substrate ketone) and an amino donor (i.e. substrate amine) are transformed into a product amine and a co-product ketone. In case $R_1$ and $R_2$ are different (and not —$NH_2$), the product amine is a chiral amine.

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints. The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

In general, the inventors have developed an efficient membrane based separation method for the separation, removal, recovery and/or enrichment of at least one amine or organic acid from a first solution, particularly from a first solution comprising a mixture of at least a first and a second amine or at least a first and a second organic acid, respectively, wherein said first and said second amine or said first and said second organic acid differ in hydrophobicity. Said separation method comprises a membrane separation step wherein an organic acid or amine of interest selectively passes a hydrophobic membrane, particularly a non-liquid, porous inorganic hydrophobic membrane, into a second solution, in combination with means or measures to avoid back-extraction or back-crossing of the separated compound from the second to the first solution, particularly a pH dependent means to avoid back-extraction. Said membrane based separation method comprises contacting a first solution comprising at least one organic acid or amine or comprising a mixture of at least two organic acids or at least two amines differing in hydrophobicity with a hydrophobic membrane, in particular a non-liquid, porous inorganic hydrophobic membrane, thus allowing the separation of an organic acid or amine in a solution or mixture according to the hydrophobic character of said organic acid or amine, with the more hydrophobic organic acid or amine passing the membrane into a second solution, wherein the pH value of said second solution is selected so that the more hydrophobic organic acid or amine is essentially in its charged state (i.e. carboxylate or ammonium form). Surprisingly, the inventors found that only the more hydrophobic amine or organic acid from a mixture of at least two amines or organic acids, differing in hydrophobicity, passes the porous inorganic hydrophobic membrane, without concomitant aqueous solvent transport in case the first solution is an aqueous solution, despite the presence of pores, and, hence, said more hydrophobic organic acid or amine can be selectively recovered from said mixture.

Accordingly, in particular embodiments, membrane based methods are provided for the separation of at least one amine from a first solution comprising at least one amine, particularly a solution comprising at least a first and a second amine differing in hydrophobic properties, wherein said method comprises the steps of:

(i) contacting said first solution comprising said at least one amine with a hydrophobic membrane, particularly a non-liquid, porous inorganic hydrophobic membrane as described herein; and (ii) extracting an amine from said first solution comprising at least one amine into a second solution across said hydrophobic membrane, wherein said hydrophobic membrane separates said first solution and said second solution and wherein said second solution is adapted or selected to limit or to avoid back-extraction, or stated differently, to limit or avoid said amine passing back across the membrane into the first solution, such as by providing a second solution with a suitable pH value to obtain said extracted amine in its charged state.

In particular embodiments, said first solution comprises a chiral amine. Preferably, said chiral amine is extracted from said first solution into a second solution across said hydrophobic membrane.

Accordingly, in other particular embodiments, membrane based methods are provided for the separation of at least one organic acid from a first solution comprising at least one organic acid, particularly a solution comprising at least a first and a second organic acid differing in hydrophobic properties, wherein said method comprises the steps of:

(i) contacting said first solution comprising said at least one organic acid with a hydrophobic membrane, particularly a non-liquid, porous inorganic hydrophobic membrane as described herein; and (ii) extracting an organic acid from said first solution comprising at least one organic acid into a second solution across said hydrophobic membrane, wherein said hydrophobic membrane separates said first solution and said second solution and wherein said second solution is adapted or selected to limit or to avoid back-extraction, or stated differently, to limit or avoid said organic acid passing back across the membrane into the first solution, such as by providing a second solution with a suitable pH value to obtain the extracted organic acid in its charged state.

As used herein, compounds, in particular organic acids or amines, differing in hydrophobic properties relate to compounds, in particular organic acids or amines, having a different log P value, in particular having a different (octanol/water) log P value (corresponding to the octanol/water partition ratio). The higher the log P value of a compound, the higher its octanol/water partition ratio and the more hydrophobic the compound is.

Accordingly, in particular embodiments, the present invention relates to methods for the separation of at least one first amine from at least one different amine differing in log P value, wherein a mixture comprising said at least one first and said at least one different amine is contacted with a hydrophobic membrane as envisaged herein, particularly a non-liquid, porous inorganic hydrophobic membrane as envisaged herein, thereby fractionating the mixture into permeating compounds comprising or enriched in said at least one first amine having a higher log P value, and a retentate comprising or enriched in said at least one different amine having a lower log P value.

Accordingly, in particular embodiments, the present invention relates to methods for the separation of at least one first organic acid from at least one different organic acid differing in log P value, wherein a mixture comprising said at least one first and said at least one different organic acid is contacted with a hydrophobic membrane as envisaged herein, particularly a non-liquid, porous inorganic hydrophobic membrane as envisaged herein, thereby fractionating the mixture into permeating compounds comprising or enriched in said at least one first organic acid having a higher log P value, and a retentate comprising or enriched in said at least one different organic acid having a lower log P value.

Log P values of many compounds are known to the skilled person. Likewise, determination of the log P value of a compound, particularly an amine, is known to the skilled person. Preferably, the compound is dissolved in a volume of octanol and water, followed by measuring the concentration of the compound in each solvent by e.g. UV/VIS spectroscopy. Alternatively, log P values can be determined via high-performance liquid chromatography, wherein the log P of a compound can be determined by correlating the retention time of said compound with similar compounds with known log P values. Advantageously, amines or organic acids differing in log P values but having similar or about the same pKa values can be separated with the methods envisaged herein.

In particular embodiments, said first solution is an aqueous solution, preferably having a pH close to the pKa value of the organic acid or amine, particularly chiral amine, with the pH value differing from the pKa value by e.g. about 2.0 units or less, preferably by 1.0 unit or less or by about 0.5 unit or less.

In particular embodiments for the separation of an amine, such as a chiral amine, said first solution is an aqueous solution with a pH value between 7.0 and 13.0, such as between 7.0 and 12.0, more preferably between pH 8.0 and 11.0 or between pH 8.5 and pH 10.0 or pH 11.0. Advantageously, the alkaline character of the first solution influences the ratio of charged vs uncharged amines (in the context of transaminase reactions, as described below, of both the donor amine and the chiral amine).

Surprisingly, the use of an aqueous solution advantageously resulted in only the amine or organic acid passing the porous non-liquid hydrophobic inorganic membrane as described herein, without a transport of solvent (i.e. water) through the pores of the membrane.

In other particular embodiments, said first solution is an organic solution. Advantageously, the use of an organic solution may favour the solubility of the organic compounds, particularly hydrophobic compounds. Suitable organic solvents include but are not limited to alkyl alcohols, such as methanol or ethanol, or liquid alkanes and hydrocarbons, such as pentane, hexane, heptane, isooctane and the like.

Importantly, in particular embodiments, said second solution is selected or adapted to avoid the back-extraction of said amine or chiral amine of interest from the second solution into the first solution across said membrane. In particular embodiments said second solution is an aqueous solution having a pH at least 2 or at least 3 units below the pKa value of the amine, such as chiral amine. In particular embodiments, said second solution is an acidic solution having a pH between 2.0 and pH 6.0, preferably having a pH between about pH 2.5 and about pH 4.0 or 5.0. Advantageously, in acid conditions, the amine or chiral amine of interest is protonated and will be retained by the hydrophobic membrane as described herein. Suitable second solutions include but are not limited to citrate or acetate buffered solutions.

It is understood that, in other particular embodiments, when the separation of organic acids is considered, in particular embodiments said second solution is an aqueous solution having a pH at least 2 or at least 3 units above the pKa value of the organic acid to obtain the organic acid in its dissociated (charged) form. Accordingly, in particular embodiments for the hydrophobic membrane based separation of an organic acid as envisaged herein, said second solution is an alkaline solution having a pH between 8.0 and pH 12.0, preferably having a pH between about pH 9 or 10 and pH 12.

In the context of the present invention, the hydrophobic membrane, particularly the non-liquid porous hydrophobic membrane as envisaged herein comprises a hydrophobic semipermeable structure, which allows separation of a first solution or mixture comprising compounds into (a) permeating compounds, particularly hydrophobic (uncharged) compounds, i.e. the one or more compounds of said mixture passing through the membrane, and (b) a retentate, i.e. the compounds of said first solution or mixture, particularly the less hydrophobic or charged compounds, that are rejected or retained by the membrane.

The hydrophobicity of the membrane can be assessed in various ways, as known by the skilled person, e.g. via contact angle measurement or flux measurements. In certain embodiments, a hydrophobic membrane as envisaged herein has a water contact angle larger than about 70°, more preferably larger than about 100° or about 110°, such as larger than about 120° or 130°. In particular embodiments, the hydrophobic membrane as envisaged herein has a water contact angle ranging from 70° to 130°. In other particular embodiments, a hydrophobic membrane as envisaged herein has a very low water flux across the membrane, preferably a water flux of about zero, at low transmembrane pressure (e.g. up to 2 or 3 bar).

In particular, said membrane is a porous membrane or a filtration membrane, such as a microfiltration, ultrafiltration or nanofiltration membrane, said porous membrane having a pore size ranging from 0.5 nm to about 100 or 200 nm, more preferably having a pore size ranging from about 0.5 to about 30, 40 or 50 nm, even more preferably ranging from about 0.5 or 1 nm to about 5, 10 or 20 nm, as measured by permporometry or nitrogen sorption techniques as known by the skilled person in the art.

In preferred embodiments, said hydrophobic membrane is a hydrophobic inorganic membrane, particularly a porous hydrophobic inorganic membrane.

In particular embodiments, said hydrophobic membrane is a non-liquid membrane, i.e. is not a liquid membrane, particularly is not a supported liquid membrane. As used herein, the term "liquid membrane" refers to a membrane comprising a liquid phase wherein the liquid phase serves as a membrane barrier between two (aqueous) solutions or gas mixtures. The liquid phase can occur in supported or unsupported form. A liquid membrane in supported form ("immobilized or supported liquid membrane") is made of a rigid porous matrix, wherein the pores are filled with an organic (hydrophobic) liquid.

Alternatively, said hydrophobic membrane may be a hydrophobic polymeric (organic) membrane, as known in the art, wherein said hydrophobic membrane is stable in the solvents and conditions used in particular embodiments, particular stable in the specific solvents used in the first and second solutions. For instance, said hydrophobic membrane can be a crosslinked polymeric membrane for improving its stability, Alternatively, said hydrophobic membrane may be a hydrophobic mixed matrix membrane.

In the context of the present invention, a particularly preferred hydrophobic membrane is a porous, inorganic membrane or ceramic membrane functionalized with an organic moiety to modify the hydrophobic character of the membrane, as further described herein, and having a pore size ranging from 0.5 nm to about 100 or 200 nm, more preferably having a pore size ranging from about 0.5 to about 30, 40 or 50 nm, even more preferably ranging from about 0.5 or 1 nm to about 5, 10 or 20 nm, as measured by permporometry or nitrogen sorption techniques as known by the skilled person in the art. Advantageously, an inorganic or ceramic membrane is chemically inert and exhibits high mechanical, thermal and hydrothermal stabilities, favoring a long term use of the chiral amine production. In addition, by varying the functional organic moiety, the hydrophobic inorganic membrane can be tailored according to the amine, preferably chiral amine, or organic acid of interest.

As used herein, the term "functionalisation", particularly in the context of functionalisation of an inorganic membrane with an organic functional group, typically refers to the chemical modification of the inorganic membrane, particularly wherein an organic functional group is linked to said inorganic membrane. In particular embodiments, "functionalisation" refers to chemical surface modification, wherein "surface" as used herein is understood to comprise the (macroscopic) outer surface of the inorganic membrane as well as the inner pore surfaces of the matrix making up the inorganic membrane. The surface to which an organic functional group is adhered may thus be an external surface and/or an internal surface of the membrane. Surface modification typically involves the replacement of hydroxyl (—OH) groups provided on the surface of the inorganic membrane by organic functional groups. Thus, the terms "organically functionalized inorganic matrix/membrane" or simply "functionalized inorganic matrix/membrane" as used herein refers to an inorganic matrix of which the (surface) properties have been changed or modified (functionalized) by covalently binding an organic group thereto. In the context of the present application, the functionalization results in a functionalized matrix or membrane which is more hydrophobic (i.e. less hydrophilic) compared to the matrix or membrane before functionalization (non-functionalized or native matrix or membrane).

In particular embodiments, the hydrophobic inorganic membranes as envisaged herein comprise an inorganic matrix comprising an oxide and/or hydroxide of an element M1, wherein M1 is a metal or silicon, functionalized with a hydrophobic organic functional group $R^1$ ($R^{1'}$) or $R^{10}$. The term "inorganic matrix" as used herein, may refer to metal (M1) oxides and/or hydroxides as such or in the form of a membrane.

In particular embodiments, M1 is selected from the group consisting of titanium, zirconium, aluminium, silicon, strontium, yttrium, lanthanum, hafnium, thorium, iron, manganese, or combinations thereof. In preferred embodiments, M1 is Si, Al, a transition metal of group 4 of the IUPAC periodic table, preferably Ti or Zr, or a mixture thereof. Preferably, the inorganic membrane is preferably made of titanium oxide and/or zirconium oxide.

In particular embodiments, the functional group $R^1$ or $R^{1'}$ is selected from the group consisting of $C_1$-$C_{16}$alkyl, $C_6$-$C_{16}$aryl, $C_7$-$C_{16}$alkylaryl, $C_7$-$C_{16}$arylalkyl, —$R^7[OR^8]_nR^9$, $C_3$-$C_8$cycloalkyl, $C_3$-$C_8$cycloalkenyl, $C_4$-$C_{10}$cycloalkylalkyl, $C_4$-$C_{10}$cycloalkenylalkyl, $C_2$-$C_{12}$alkenyl, 3- to 8-membered heterocyclyl, 5- to 10-membered heteroaryl, heterocyclyl$C_1$-$C_6$alkyl, heteroaryl$C_1$-$C_4$alkyl and $C_2$-$C_{12}$alkynyl; wherein $R^7$ and $R^8$ are independently from each other $C_1$-$C_4$alkylene; n is an integer from 1 to 4; and $R^9$ is $C_1$-$C_4$ alkyl; In particular embodiments, the functional group $R^{10}$ is selected from the group consisting of $C_1$-$C_8$ alkylene, $C_6$-$C_{10}$arylene, $C_7$-$C_{16}$alkylarylene, $C_7$-$C_{16}$arylalkylene, —$R^{11}[OR^{12}]_m$ $R^{13}$—, $C_3$-$C_8$cycloalkylene, $C_3$-$C_8$cycloalkenylene, $C_4$-$C_{10}$cycloalkylalkylene, $C_4$-$C_{10}$cycloalkenylalkylene, $C_2$-$C_{12}$alkenylene, 3- to 8-membered heterocyclylene, 5- to 10-membered heteroarylene, heterocyclyl$C_1$-$C_6$alkylene, heteroaryl$C_1$-$C_4$alkylene and $C_2$-$C_{12}$alkynylene; wherein $R^{11}$, $R^{12}$, and $R^{13}$ are independently from each other $C_{1-4}$alkylene;

wherein $R^1$ ($R^{1'}$) and $R^{10}$ are optionally substituted with one or more groups independently selected from hydroxyl, —$OR^4$, amino, halo, sulfhydryl, —$SR^5$, and —$COOR^6$; wherein $R^4$, $R^5$, $R^6$ are independently selected from $C_1$-$C_6$alkyl, halo and $C_6$-$C_{10}$aryl, and m is an integer from 1 to 4.

In particularly preferred embodiments, the moiety $R^1$ ($R^{1'}$) or $R^{10}$ is selected from the group comprising (a) haloalkyl, preferably fluoroalkyl or perfluoroalkyl, more preferably fluoro$C_1$-$C_{16}$alkyl or perfluoro$C_1$-$C_{16}$alkyl, more preferably fluoro$C_1$-$C_8$alkyl or (per)fluoro$C_1$-$C_8$alkyl; (b) aryl, preferably $C_6$-$C_{16}$aryl, more preferably $C_6$-$C_{10}$aryl; and (c) haloaryl, preferably fluoroaryl or perfluoroaryl, more preferably fluoro$C_6$-$C_{16}$aryl or perfluoro$C_6$-$C_{16}$aryl, more preferably fluoro$C_6$-$C_{10}$aryl or perfluoro$C_6$-$C_{10}$aryl. $R^1$ or $R^{10}$ moieties as used herein may comprise linear, branched or cyclic molecules.

The term "alkyl" by itself or as part of another substituent, refers to a straight or branched saturated hydrocarbon group joined by single carbon-carbon bonds.

When a subscript is used herein following a carbon atom, the subscript refers to the number of carbon atoms that the named group may contain. Thus, for example, "$C_1$-$C_4$alkyl" means an alkyl of one to four carbon atoms. Examples of $C_1$-$C_4$alkyl groups are methyl, ethyl, propyl, isopropyl, butyl, isobutyl and tert-butyl.

As used herein, the term "$C_1$-$C_x$alkylene", by itself or as part of another substituent, refers to $C_1$-$C_x$alkyl groups that are divalent, i.e., with two single bonds for attachment to two other groups. Alkylene groups may be linear or branched and may be substituted as indicated herein.

In a particular embodiment, $R^1$ is $C_3$-$C_8$cycloalkyl. As used herein, the term "$C_3$-$C_8$cycloalkyl", by itself or as part of another substituent, refers to a saturated cyclic alkyl group containing from about 3 to about 8 carbon atoms. Examples of $C_3$-$C_8$cycloalkyl include cyclopropyl, cyclobutyl, cyclopentyl, or cyclohexyl, cycloheptyl and cyclooctyl.

In a particular embodiment, $R^1$ is $C_3$-$C_8$cycloalkenyl. As used herein, the term "cycloalkenyl" by itself or as part of another substituent, refers to a non-aromatic mono- or multicyclic ring system comprising about 3 to 8 carbon atoms, preferably about 5 to 8 carbon atoms, which contains at least one carbon-carbon double bond. Preferred cycloalkenyl rings contain 5 or 6 ring atoms, such as cyclopentenyl and cyclohexenyl. In a particular embodiment, $R^1$ is a $C_6$-$C_{10}$aryl. As used herein, the term "$C_6$-$C_{10}$aryl", by itself or as part of another substituent, refers to a polyunsaturated, aromatic hydrocarbyl group having a single ring (i.e. phenyl) or multiple aromatic rings fused together (e.g. naphthalene), or linked covalently, typically containing 6 to 10 carbon atoms; wherein at least one ring is aromatic. Aryl rings may be unsubstituted or substituted with from 1 to 4 substituents on the ring. Examples of $C_6$-$C_{10}$aryl include phenyl, naphthyl, indanyl, or 1,2,3,4-tetrahydro-naphthyl.

In a particular embodiment, $R^1$ is $C_2$-$C_{12}$alkenyl, preferably $C_2$-$C_6$alkenyl. The term "alkenyl" by itself or as part of another substituent, refers to an unsaturated hydrocarbyl group, which may be linear, or branched, comprising one or more carbon-carbon double bonds. Non-limiting examples of $C_2$-$C_6$alkenyl groups include ethenyl, 2-propenyl, 2-butenyl, 3-butenyl, 2-pentenyl and its chain isomers, 2-hexenyl and its chain isomers, 2,4-pentadienyl and the like.

In a particular embodiment, $R^1$ is $C_2$-$C_{12}$alkynyl, preferably $C_{2-C6}$alkynyl. The term "alkynyl" by itself or as part of another substituent, refers to an unsaturated hydrocarbyl group, which may be linear, or branched, comprising one or more carbon-carbon triple bonds. Non limiting examples of $C_2$-$C_6$alkynyl groups include ethynyl, 2-propynyl, 2-butynyl, 3-butynyl, 2-pentynyl and its chain isomers, 2-hexynyl and its chain isomers and the like.

In a particular embodiment, $R^1$ is heterocyclyl, preferably a 3- to 8-membered heterocyclyl. The terms "heterocyclyl" or "heterocyclo" as a group or part of a group, refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected N, O and/or S, where the N and S, where the N and S heteroatoms may be oxidized and the N heteroatoms may be quaternized. The heterocyclic group may be attached at any heteroatom or carbon atom of the ring or ring system, where valence allows. The rings of multi-ring heterocycles may be fused, bridged and/or joined through one or more spiro atoms. A "substituted heterocyclyl" refers to a heterocyclyl group having one or more substituent(s) (for example 1, 2 or 3 substituent(s), or 1 to 2 substituent(s)), at any available point of attachment. Non limiting exemplary heterocyclic groups include oxiranyl, pyrrolidinyl, tetrahydrofuranyl, tetrahydrothiophenyl, dihydropyrrolyl, dihydrofuranyl, imidazolidinyl, pyrazolidinyl, imidazolinyl, pyrazolinyl, oxazolidinyl, isoxazolidinyl, oxazolinyl, isoxazolinyl, thiazolidinyl, isothiazolidinyl, thiazolinyl, piperidyl, tetrahydropyranyl, indolinyl, piperazinyl, 3-dioxolanyl, 1,4-dioxanyl, 1,3-dioxolanyl, and 1,4-oxathianyl.

In particular embodiments, $R^1$ is heteroaryl. The term "heteroaryl", as used herein, represents a stable 5- to 10-membered aromatic ring system which consists of carbon atoms and from one to four heteroatoms selected from the group consisting of N, O and S, and wherein the nitrogen and sulfur heteroatoms may optionally be oxidized, and the nitrogen heteroatom may optionally be quaternized. Preferably, said heteroaryl is a 5- to 6-membered aromatic ring. Examples of such heteroaryl groups include, but are not limited to, furan, furazan, imidazole, isothiazole, isoxazole, oxadiazole, oxazole, pyrazine, pyrazole, pyridazine, pyridine, pyrimidine, pyrrole, tetrazole, thiadiazole, thiazole, thiophene, triazine, triazole, and N-oxides thereof. Preferably said heteroaryl is furan.

The term "$C_7$-$C_{16}$aralkyl" or "$C_7$-$C_{16}$arylalkyl", as a group or part of a group, means an aryl-alkyl in which the aryl and alkyl are as previously described, wherein the aryl and alkyl together contain 7 to 16 carbon atoms. The bond to the parent moiety is through the alkyl. Examples of $C_7$-$C_{16}$aralkyl radicals include benzyl, phenethyl, 3-(2-naphthyl)-butyl, and the like.

The term "$C_7$-$C_{16}$alkylaryl", as a group or part of a group, means an alkyl-aryl in which the aryl and alkyl are as previously described, wherein the aryl and alkyl together contain 7 to 16 carbon atoms. The bond to the parent moiety is through the aryl. A non-limiting example of a $C_7$-$C_{16}$alkylaryl is tolyl.

In particular embodiments, $R^1$ is heterocyclyl$C_{1-6}$alkyl. The term "heterocyclyl$C_{1-6}$alkyl", as a group or part of a group, means a $C_{1-6}$alkyl as defined herein, wherein at least one hydrogen atom is replaced by at least one heterocyclyl as defined herein, more particularly a 3- to 8-membered heterocyclyl, more particularly a 3- to 6-membered heterocyclyl, and even more particularly a 3- to 5-membered heterocyclyl.

In particular embodiments, $R^1$ is heteroaryl$C_1$-$C_6$alkyl. The term "heteroaryl$C_1$-$C_6$alkyl", as a group or part of a group, means a $C_1$-$C_6$alkyl as defined herein, wherein at least one hydrogen atom is replaced by at least one heteroaryl as defined herein, more particularly a 5- to 10-membered heteroaryl, more particularly a 5- to 6-membered heteroaryl. The bond to the parent moiety is through the alkyl.

In particular embodiments, $R^1$ is $C_4$-$C_{10}$cycloalkylalkyl, more particularly $C_4$-$C_8$cycloalkylalkyl. The term "$C_4$-$C_{10}$cycloalkylalkyl" as a group or part of a group, means an cycloalkyl-alkyl in which the cycloalkyl and alkyl are as previously described, wherein the cycloalkyl and alkyl together contain 4 to 10 carbon atoms. The bond to the parent moiety is through the alkyl. Examples of $C_4$-$C_{10}$cycloalkylalkyl radicals include cyclopropylmethyl, cyclopropylethyl, cyclopropylpropyl, cyclopentylmethyl, cyclopentylethyl, cyclopentylpropyl, cyclohexylmethyl, cyclohexylethyl, and cyclohexylpropyl.

In a particular embodiment, $R^1$ is $C_4$-$C_{10}$cycloalkenylalkyl. As used herein, the term "$C_4$-$C_{10}$cycloalkenylalkyl" as a group or part of a group, means an cycloalkenyl-alkyl in which the cycloalkenyl and alkyl are as defined herein, wherein the cycloalkenyl and alkyl together contain 4 to 10 carbon atoms. The bond to the parent moiety is through the alkyl.

In particular embodiments, $R^{10}$ is $C_{1-8}$alkylene. In further embodiments, $R^{10}$ is $C_{1-6}$alkylene, more particularly $C_{1-4}$alkylene. Non-limiting examples of $C_{1-6}$alkylene groups include methylene (—$CH_2$—), ethylene (—$CH_2$—$CH_2$—), methylmethylene (—$CH(CH_3)$—), 1-methyl-ethylene (—$CH(CH_3)$—$CH_2$—), n-propylene (—$CH_2$—$CH_2$—$CH_2$—), 2-methylpropylene (—$CH_2$—$CH(CH_3)$—$CH_2$—), 3-methylpropylene (—$CH_2$—$CH_2$—$CH(CH_3)$—), n-butylene (—$CH_2$—$CH_2$—$CH_2$—$CH_2$—), 2-methylbutylene (—$CH_2$—$CH(CH_3)$—$CH_2$—$CH_2$—), 4-methylbutylene (—$CH_2$—$CH_2$—$CH_2$—$CH(CH_3)$—), pentylene and its chain isomers, and hexylene and its chain isomers. In particular embodiments, $R^{10}$ is an ether or oligoether of formula —$R^{11}[OR^{12}]_m R^{13}$—, wherein $R^{11}$, $R^{12}$ and $R^{13}$ are independently from each other $C_{1-4}$alkylene; and m is an integer from 1 to 4. In further embodiments, $R^{11}$, $R^{12}$ and $R^{13}$ are independently from each other $C_{1-3}$alkylene; and m is an integer from 1 to 3.

In particular embodiments, $R^{10}$ is $C_3$-$C_8$cycloalkylene. As used herein, the term "cycloalkylene", by itself or as part of another substituent, refers to a cycloalkyl moiety as defined herein which is divalent.

In a particular embodiment, $R^{10}$ is $C_3$-$C_8$cycloalkenylene. As used herein, the term "cycloalkenylene" by itself or as part of another substituent, refers to a cycloalkenyl as defined herein, which is divalent. Preferred cycloalkenylene rings contain 5 or 6 ring atoms, such as cyclopentenylene and cyclohexenylene.

In particular embodiments, $R^{10}$ is $C_6$-$C_{10}$arylene. As used herein, the term "arylene", by itself or as part of another substituent, refers to an aryl moiety as defined herein which is divalent.

In particular embodiments, $R^{10}$ is $C_2$-$C_{12}$alkenylene, preferably $C_2$-$C_6$alkenylene. The term "alkenylene" by itself or as part of another substituent, refers to an alkenyl moiety as defined herein, which is divalent.

In particular embodiments, $R^{10}$ is $C_2$-$C_{12}$alkynylene, preferably $C_2$-$C_6$alkynylene. The term "alkynylene" by itself or as part of another substituent, refers to an alkynyl moiety as defined herein, which is divalent.

In particular embodiments, $R^{10}$ is heterocyclylene, preferably a 3- to 8-membered heterocyclylene. The term "heterocyclylene" as a group or part of a group, refers to a heterocyclyl moiety as defined herein, which is divalent.

In particular embodiments, $R^{10}$ is heteroarylene. The term "heteroarylene", as used herein, refers to a heteroaryl moiety as defined herein, which is divalent.

In particular embodiments, $R^{10}$ is $C_7$-$C_{16}$aralkylene. The term "aralkylene" as a group or part of a group, refers to an aralkyl moiety as defined herein, which is divalent.

In particular embodiments, $R^{10}$ is "$C_7$-$C_{16}$alkylarylene". The term "alkylarylene", as a group or part of a group, refers to an alkylarylene as defined herein, which is divalent.

In particular embodiments, $R^{10}$ is heterocyclyl$C_1$-$C_6$alkylene. The term "heterocyclyl$C_1$-$C_6$alkylene", as a group or part of a group, refers to a heterocyclyl$C_1$-$C_6$alkyl moiety as defined herein, which is divalent.

In particular embodiments, $R^{10}$ is heteroaryl$C_1$-$C_6$alkylene. The term "heteroaryl$C_1$-$C_6$alkylene", as a group or part of a group, refers to a heteroaryl$C_1 C_6$alkyl as defined herein, which is divalent.

In particular embodiments, $R^{10}$ is $C_4$-$C_{10}$cycloalkylalkylene, more particularly $C_4$-$C_8$cycloalkylalkylene. The term "cycloalkylalkylene" as a group or part of a group, refers to a cycloalkylalkylene as defined herein, which is divalent.

In a particular embodiment, $R^{10}$ is $C_4$-$C_{10}$cycloalkenylalkylene. As used herein, the term "$C_4$-$C_{10}$cycloalkenylalkylene" as a group or part of a group, means an cycloalkenylalkylene in which the cycloalkenyl and alkylene are as defined herein, wherein the cycloalkenyl and alkylene together contain 4 to 10 carbon atoms.

The term "halo" or "halogen" as used herein refers to fluoro, chloro, bromo or iodo.

The term "amino" by itself or as part of another substituent, refers to —$NH_2$.

The term "hydroxyl" by itself or as part of another substituent, refers to —OH.

The term "sulfhydryl", by itself or as part of another substituent, refers to an —SH group.

The term "cyano", by itself or as part of another substituent, refers to an —CN group.

The term "phosphonate" as used herein includes phosphonic acids, and esters or salts thereof. The term "phosphinate" as used herein includes phosphinic acids, and esters or salts thereof.

The term "aryl" is intended to encompass monocyclic, polycyclic or heterocyclic aryl.

The term "haloalkyl" is intended to encompass alkyl as defined herein substituted with one or more halogen atoms. The term "(per)fluoroalkyl" is intended to encompass alkyl as defined herein substituted with one or more fluor atoms. The term "haloaryl" is intended to encompass aryl as defined herein substituted with one or more halogen atoms, preferably substituted with between 1 and 5 halogen atoms. The term "(per)fluoroaryl" is intended to encompass aryl as defined herein substituted with one or more fluor atoms, preferably substituted with between 1 and 5 fluor atoms. The term "substituted" is used to indicate that one or more hydrogens on the moiety indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture.

In particular embodiments, the organic functional group $R^1$ ($R^{1'}$) or $R^{10}$ is linked to the inorganic membrane, particularly on the external and/or internal surface of said membrane via a direct M1-$R^1$ bond; an M1-O—P—$R^1$ bond; a M1-O—Si—$R^1$ bond; a M1-O—P—$R^{10}$—P—O-M1 bond or a M1-O—Si—$R^{10}$—Si—O-M1 bond.

Various methods have been reported for the surface-modification of ceramic membranes, particularly porous ceramic membranes, including methods involving for instance co-condensation reactions, grafting reactions with organosilane or phosphonic acids, polymerization reactions on the surface etc. Thus, in particular embodiments the membrane (surface) is reacted with an organometallic reagent, a phosphonate, a phosphinate or an organosilane comprising said organic moiety $R^1$ ($R^{1'}$) or $R^{10}$.

In particular embodiments, functionalization of the inorganic membrane with an organic functional group occurs via reaction with an organometallic reagent, such as a Grignard reagent and/or an organolithium reagent. A preferred procedure for the functionalization of an inorganic matrix via reaction with organometallic chemistry is based on the method for obtaining a functionalized matrix as described in international patent application WO2010/106167, which is hereby incorporated by reference. Thus, in certain embodiments, the reaction of the inorganic matrix as envisaged herein with the organometallic reagent comprises an appropriate pretreatment of the inorganic matrix, including drying the matrix; reacting the dried matrix in the presence of a dry solvent with said organometallic reagent, thereby obtaining a functionalized matrix; and optionally, washing and drying the functionalized matrix. The functionalization via reaction with an organometallic compound as described in WO2010/106167 results in the functionalization of the matrix with one or more organic functional groups, as defined herein, that are directly bound covalently to an element M1 as envisaged herein on a surface of said matrix via a direct M1-carbon bond, i.e. not including an oxygen bridge. Organometallic reagents as used herein may be represented by formula $R^1$-M2, or formula $R^1$-M2-X, or formula $R^1$-M2-$R^{1'}$, wherein $R^1$ and $R^{1'}$ can be different or identical, M2 is a metal selected from group 1 or 2 of the IUPAC periodic table, more particularly selected from Li and/or Mg, and wherein X is a halogen atom, and preferably Br, Cl or I.

In particular embodiments, functionalization of the inorganic membrane with an organic functional group occurs via reaction with a phosphonate and/or a phosphinate. Various procedures for the functionalization of an inorganic matrix via a (condensation) reaction with phosphonates which are suitable for use in the present method are known in the art. An example of a suitable procedure is the one described in patent application US 2002/0023573, which is hereby incorporated by reference. The functionalization via reaction with an phosphonate or phosphinate as described therein results in the functionalization of the matrix with an organic functional group $R^1$ or $R^{10}$ as defined herein, that are bound covalently to a metal M1 on a surface of said inorganic matrix via a covalent M1-O—P—$R^1$ bond or M1-O—P—$R^{10}$—P—O-M1, more particularly via a covalent M1-O—P—C bond. With phosphonates, the same phosphorous atom may be bound to the matrix via a mono-, bi-, or tridentate bond (i.e. via one, two, or three P—O-M1 bonds). The M1-O—P-carbon bond typically provides sufficient stability for use of the functionalized inorganic membrane in filtration, for cleaning of the material, etc.

In particular embodiments, functionalization of the inorganic membrane with an organic functional group occurs via reaction with an organosilane reagent. Reaction of the inorganic matrix with an organosilane results in the functionalization of the matrix with an organic functional moiety $R^1$ or $R^{10}$ which is bound covalently to a metal M1 as envisaged herein, particularly on a surface of said matrix via a covalent M1-O—Si—$R^1$ bond or a M1-O—Si—$R^{10}$—Si—O-M1 bond, more particularly via a covalent M1-O—Si—C bond. The M1-O—Si-carbon bond typically is less stable than a direct M1-carbon bond if M1 is a non-silicon metal. However, if M1 is silicon, the M1-O—Si-carbon bond provides an excellent stability. Thus, in certain embodiments, the organic functional group $R^1$ or $R^{10}$ is bound covalently to M1 via a covalent M1-O—Si-carbon bond, provided that M1 is silicon. Various procedures for the functionalization of an inorganic matrix via a (condensation) reaction with organosilanes which are suitable for use in the present method are known in the art. An example of a suitable procedure is the one described in patent application US 2006/237361, which is hereby incorporated by reference.

It is noted that where the functional organic group $R^1$ ($R^{1'}$) or $R^{10}$ comprises a functional group which is not compatible with the functionalization process (via reaction with organometallic reagents or phosphonates), such group should be provided in a protected form (i.e. with a protecting group), that is to be removed after functionalization. Protecting groups, and the methods for removing them are well known in the art and will not be disclosed in detail herein.

In particular embodiments, the inorganic membrane functionalized with an organic functional group as envisaged herein is a membrane comprising a (macro)porous support coated with at least one separating membrane layer made of an oxide and/or hydroxide of M1 at the surface with the separating membrane layer functionalized with an organic functional group.

In certain embodiments, the inorganic matrix comprising the metal M1 as envisaged herein, are provided as particles in a mixed matrix membrane. For example, the particles may be embedded in a polymer matrix. The preparation of mixed matrix membranes and the selection of the size and amount of particles and (polymer) matrix material are well-known in the art, depending on the required characteristics of the membranes.

The membrane based separation method of hydrophobic amines according to particular embodiments of the present invention is particularly useful in the transaminase catalysed production and separation of chiral amines. Accordingly, in particular embodiments, the present invention provides a method to obtain a chiral amine, wherein a transaminase catalysed transamination of an amino donor and amino acceptor is combined with a hydrophobic membrane separation, preferably the non-liquid porous inorganic hydrophobic membrane based separation as envisaged herein, of the produced chiral amine, particularly wherein the chiral amine passes the hydrophobic membrane as described herein, into a second solution (also referred to as the "collection solution"), preferably an acidic aqueous (second) solution. This efficient process allows to obtain chiral amines in high yield. Indeed, the hydrophobic membrane based separation, in particular using a porous, non-liquid inorganic hydrophobic membrane, as described herein, can be used to separate the (more hydrophobic) chiral amine from the (less hydrophobic) amino donor, thus selectively removing the chiral amine from the reaction mixture. Advantageously, the selective removal of the product amine influences the reaction equilibrium of the transaminase reaction and promotes further transformation of the amino acceptor into the product amine. Also, removal of the product amine avoids or limits product inhibition of the transaminase reaction, allowing the transamination reaction to be performed with lower solvent load and improved process mass intensity (PMI).

Accordingly, in particular embodiments, the present invention relates to a method for obtaining a chiral amine comprising the steps of (a) performing a transamination reaction with a transaminase, preferably an (R) or (S) selective transaminase, in a first solution (also referred to as "reaction solution") comprising a prochiral amino acceptor and an amino donor, thus forming a chiral amine in said first solution; and (b) contacting said first solution with a hydrophobic membrane, preferably a porous inorganic hydrophobic membrane functionalized with an organic group, as envisaged herein and extracting the chiral amine from the first solution into a second solution or collection solution as envisaged herein across said hydrophobic membrane, wherein said hydrophobic membrane separates said first solution and said second solution. Preferably, the pH value of said second solution is selected so that the chiral amine, extracted from the first solution, is essentially in its charged state, thus avoiding back extraction of said chiral amine.

In particular embodiments, said membrane is a porous, inorganic membrane, which is functionalized with a chiral organic moiety, allowing to separate the desired chiral amine enantiomer from the undesired chiral enantiomer, when performing the transamination reaction with an enzyme having a lower enantiomer selectivity.

In particular embodiments, said first solution is an aqueous alkaline solution or a solution of an organic solvent. Advantageously, the use of an organic solvent solution may favour the solubility of the substrate ketone, and/or the chiral amine, while, surprisingly, still maintaining a high transaminase reactivity. Suitable organic solvents have been described above.

It is understood the transamination reaction for producing (optically active) chiral amines, as used herein, typically comprises the steps of
  providing an amino acceptor and an amino donor;
  reacting the amino acceptor and the amino donor with a transaminase enzyme, such as a (R) or (S)-selective transaminase; and
  obtaining the desired (optically active) chiral amine and a co-product (ketone).

"Transaminase" and "aminotransferase" are used interchangeably herein and refer to a polypeptide with enzymatic activity capable of transferring an amino group (—NH$_2$), a pair of electrons, and a proton from a primary amine to a carbonyl group (C=O) of an acceptor molecule, using pyridoxal-phosphate as a coenzyme in the transaminase reaction. Transaminases as used herein may be naturally occurring (wild type) transaminases or non-naturally occurring transaminases generated by human manipulation or engineered, such as recombinant polypeptides or variant polypeptides engineered to have a modified or improved enzymatic activity. (R) or (S)-selective transaminases are capable of catalyzing the transfer of an amino group from an amino donor to an acceptor molecule, thereby forming R-specific or S-specific chiral amines, respectively. The transaminase as used herein can be in free form, immobilized on a suitable support or matrix such as cross-linked dextran or agarose, silica, polyamide, or cellulose, or encapsulated in polyacrylamide, alginates, fibers, or the like. The transaminase as used herein may be in the form of whole cells containing transaminase, or engineered whole cells acting as a host to transaminase. Methods for such immobilization or encapsulation are known to the skilled person. In certain embodiments, the transaminase is immobilized on the hydrophobic membrane as envisaged herein. It is understood that the skilled person is able to select of an appropriate transaminase depending on the desired chiral product, and the available substrates (i.e. the ketone acceptor and the amine donor).

An "amino acceptor" refers to a carbonyl compound which accepts an amino group from an amino donor or donor amine. In a particularly preferred embodiment of the present invention the amino acceptor contains a ketone functionality and is also referred to as "acceptor ketone" or "substrate ketone". The selection of the acceptor ketone typically depends on the desired chiral amine.

The terms "amino donor", "donor amine" or "substrate amine" refer to any molecule that will react with a transaminase and an acceptor ketone by providing an amino group to the acceptor ketone. A preferred amino donor is a primary amine or an amino acid. Typical amino donors as envisaged herein include chiral and achiral amino acids, and chiral and achiral amines, including but not limited to isopropylamine, glycine, glutamic acid, glutamate, alanine, aspartic acid, lysine or aminobutane. Particularly preferred is isopropylamine (IPA), as it is a cheap and widely available compound, with low hydrophobicity, and hence will be particularly well retained by the membrane, and which, following transamination, is transformed in the volatile co-product acetone, which can be easily removed from the product stream, particularly the second solution, e.g. by distillation. In addition, due to its low hydrophobicity, IPA will easily be separated from a more hydrophobic chiral amine, even if IPA and said hydrophobic amine have similar or about the same pKa value.

In particular embodiments, the membrane based separation process, in particular the separation of an amine or organic acid, in particular a hydrophobic amine or organic acid from a first solution, and/or the membrane based chiral amine production, as envisaged herein occurs in a membrane contactor module as known by the skilled person.

Accordingly, in particular embodiments, the present invention relates to a method for obtaining an amine, particularly a chiral amine, using a membrane contactor module wherein a hydrophobic membrane as envisaged herein, particularly a porous inorganic membrane functionalized with an organic group, forms a semipermeable barrier between a first and a second compartment of the membrane contactor module, said method comprising the steps of (i) feeding a first solution comprising an amine or chiral amine to a first compartment of said membrane contactor module; and (ii) extracting the amine or chiral amine across a hydrophobic membrane, particularly a porous inorganic membrane functionalized with an organic group, as envisaged herein, to a second compartment of the membrane contactor module, wherein said second compartment comprises a second solution, as envisaged herein, particularly an acidic solution, particularly in a cross-flow setup vs the flow of the first solution.

In certain embodiments, said first solution is a solution comprising an amino donor, preferably a non-amino acid amino donor, and a prochiral amino acceptor which is contacted with a transaminase prior to or concomitant with step (i), thus forming a chiral amine in said first solution. In certain embodiments, transamination of the ketone acceptor and amino donor in said first solution may be carried out in a bioreactor using the transaminase enzyme with the substrate typically at a defined concentration. The reaction parameters such as pH, temperature, and mixing may be maintained at levels that favor optimal biocatalytic activity and stability and/or may be maintained at levels that favor optimal membrane separation of the chiral amine. A similar reaction can be done in continuous mode to recover the product on formation, to prevent reverse reaction.

In other particular embodiments, the present invention relates to a method for obtaining organic acids, using a membrane contactor module wherein a hydrophobic membrane as envisaged herein, particularly a porous inorganic membrane functionalized with an organic group, forms a semipermeable barrier between a first and a second compartment of the membrane contactor module, said method comprising the steps of (i) feeding a first solution comprising an organic acid to a first compartment of said membrane contactor module; and (ii) extracting the organic acid across said hydrophobic membrane, particularly a porous inorganic membrane functionalized with an organic group, as envisaged herein, to a second compartment of the membrane contactor module, wherein said second compartment comprises a second solution, as envisaged herein, adapted to avoid the back-extraction of the organic acid, particularly in a cross-flow setup vs the flow of the first solution.

Figure 2:
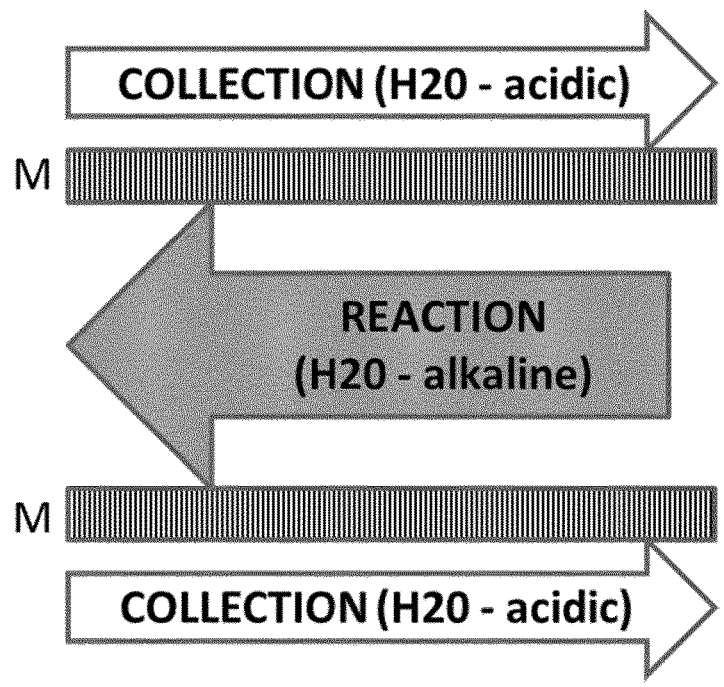
FIG. 2 schematically represents a (cross flow) membrane contactor set-up according to a particular embodiment of the present invention wherein the enzymatic transamination reaction occurs in an aqueous, alkaline solvent and wherein the chiral amines pass a hydrophobic membrane into an aqueous acidic collection liquid. M represents a membrane as envisaged herein.

Referring to FIG. 2, in particular embodiments, the hydrophobic membrane in the membrane contactor module will separate two aqueous phases, i.e. the first solution at alkaline pH values, and the second acidic solution for the collection of the amine or chiral amine. In this setup, the hydrophobic membrane, particularly a porous inorganic membrane functionalized with an organic group, acts as a selective barrier where the redistribution of the components takes place, with the more hydrophobic amine (preferably the chiral product amine) being primarily transferred across the membrane. When combined with a transaminase reaction, in this setup, the transamination preferably takes place in an aqueous alkaline solution.

Figure 3:
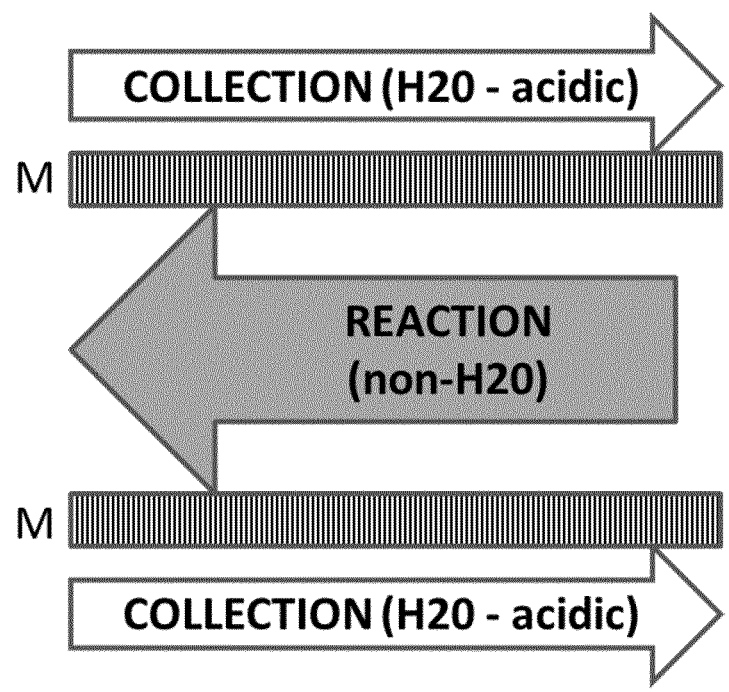
FIG. 3 schematically represents a (cross flow) membrane contactor set-up according to a particular embodiment of the present invention wherein the enzymatic transamination reaction occurs in an organic solvent and wherein the chiral amines pass a hydrophobic membrane into an aqueous acidic collection liquid. M represents a membrane as envisaged herein.

Referring to FIG. 3, in particular embodiments, the hydrophobic membrane in the membrane contactor module separates an organic and an aqueous phase, i.e. the amine is initially in an organic solvent (e.g. n-heptane), while the second acidic solution functions for the collection of the amine or chiral amine. In this setup, the hydrophobic membrane, particularly a porous inorganic membrane functionalized with an organic group, acts as a selective barrier where the redistribution of the components takes place, with the more hydrophobic amine (preferably the chiral product amine) being primarily transferred across the membrane. When combined with a transaminase reaction, in this setup, the transamination preferably takes place in an organic solvent, such as e.g. n-heptane and the resulting amines are extracted in an acidic aqueous phase.

The following examples are provided for the purpose of illustrating the claimed methods and applications and by no means are meant or should be interpreted to limit the scope of the invention.

EXAMPLES

Example 1

Figure 4:
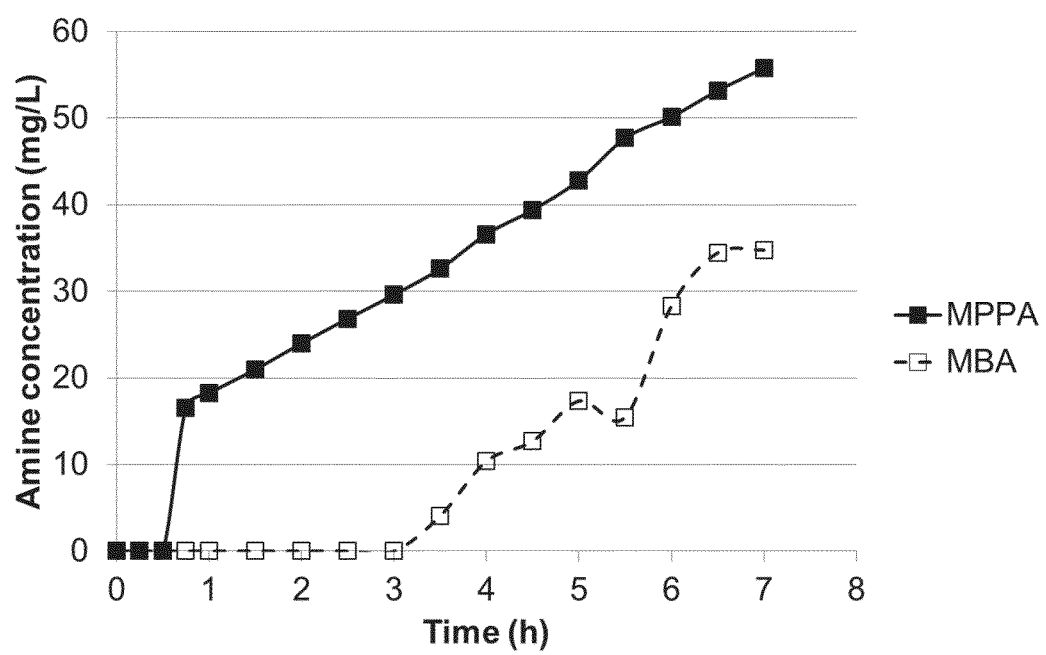
FIG. 4 represents the concentration of MPPA and MBA in the extraction or collection compartment of a membrane contactor module over time from an alkaline solution comprising MPPA and MBA, using an acidic solution as collection solution.

A mixture of MPPA and MBA in a pH 10 aqueous buffer (feed solution) was applied to a first compartment of a membrane contactor module, with the second compartment comprising a sodium acetate buffer (pH 3) (collection solution). The membrane separation was performed at a flow rate of 20 l/h, a temperature of 30° C. and a transmembrane pressure of 300-500 mbar. Feed and collection solutions were continuously recycled in the membrane contactor module. The membrane used was a phenyl phosphonic acid functionalized ceramic membrane, wherein both the external surface as the internal surface of the pores was linked to the organic moiety. The membrane before functionalization had a titanium oxide top layer with pore size of 0.9 nm. The amine concentration in the extracting sodium acetate solution was followed up over time (FIG. 4). The amines used are listed in Table 1. They have a different octanol/water partition ration (expressed as log P value).

As can be seen in FIG. 4, MPPA easily passed the membrane and MPPA could already be detected in the extracting solution after less than 1 hr of membrane extraction and showed a continuous increase over time. In contrast, MBA could only be found in the acidic extracting solution after 3.5 h of membrane extraction.

Assuming that only the uncharged amine can pass through the membrane, the (theoretical) extractable amount can be calculated using the % uncharged amine at pH 10 (Table 1). For MPPA (596 mg in feed solution) and MBA (484 mg in the feed solution) this corresponds to 113 mg and 358 mg theoretical extractable amine, respectively. After 7 h, 15% of this amount was extracted for MPPA, while only 3% of this amount was extracted for MBA.

These results indicate that the uncharged/charged ratio of the amine at the pH of the feed solution [which is greater for MBA (74:26; ≈3) vs MPPA (19:81; ≈0.25)] is not the main driving force for the membrane separation. Rather, these results indicate that the hydrophobic character of the amine (as expressed by the log P value) determines the membrane separation behaviour.

Moreover, surprisingly, no water transport was observed over the membrane, as shown by the mass balance of the experiment.

Similar results, but less pronounced, were obtained using a hexadecane phosphonic acid functionalized ceramic membrane (wherein the membrane before functionalization has a titanium oxide top layer with pore size of 0.9 nm) with only the external surface modified with the organic moiety, indicating that the hydrophobic character of both the membrane and the amine determine the separation behaviour.

Example 2

Figure 5:
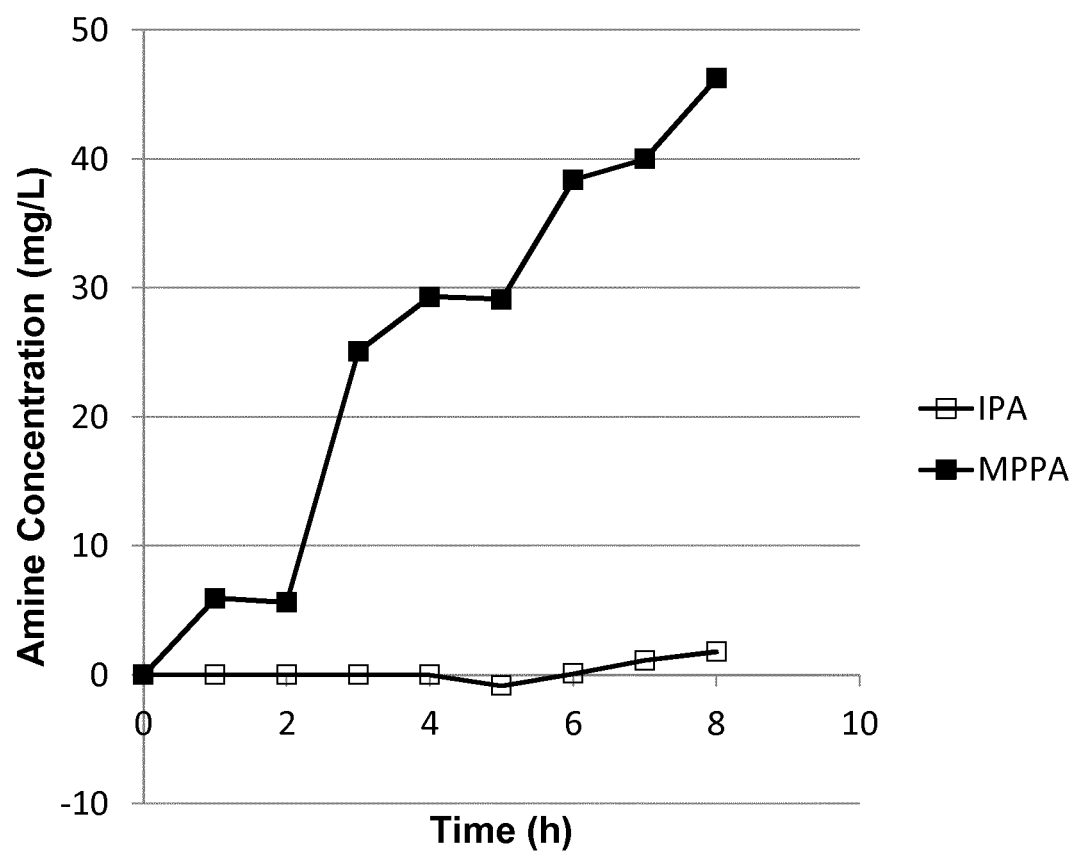
FIG. 5 represents the concentration of MPPA and IPA in the extraction or collection compartment of a membrane contactor module over time from an alkaline solution comprising MPPA and IPA, using an acidic solution as collection solution.

A mixture of isopropyl amine (IPA) and 1-methyl-3-phenylpropylamine (MPPA) in a pH 10 aqueous buffer (feed solution) was applied to a first compartment of a membrane contactor module, with the second compartment comprising a sodium acetate buffer (pH 3) (collection solution). The membrane separation was performed at a flow rate of 20 l/h, temperature of 30° C. and transmembrane pressure of 300 to 500 mbar. Feed and collection solutions were continuously recycled in the membrane contactor module. The membrane used was a phenyl phosphonic acid functionalized ceramic membrane (as in Example 1), wherein both the external surface as the internal surface of the pores was linked to the organic moiety. The amine concentration in the extracting sodium acetate solution was followed up over time (FIG. 5).

The amines used are listed in Table 2. They have a different octanol/water partition ration (expressed as log P value), but similar pKa value, and, consequently, have a similar % of uncharged amine population.

TABLE 1

|  | MPPA (*) | MBA (*) |
| --- | --- | --- |
| LogP | 2.264 | 1.7 |
| pKa | 10.63 | 9.54 |
| % uncharged at pH 10 (**) | 19 | 74 |

(*) MPPA: methyl-phenylpropylamine; MBA: methylbenzylamine;
(**) calculated using Henderson-Hasselbalch equation

TABLE 2

|  | MPPA (*) | IPA (*) |
| --- | --- | --- |
| LogP | 2.264 | 0.391 |
| pKa | 10.63 | 10.73 |
| % uncharged at pH 10 (**) | 19 | 16 |

(*) MPPA: methyl-phenylpropylamine; IPA: isopropyl amine;
(**) calculated using Henderson-Hasselbalch equation As can be seen in FIG. 5, MPPA easily passed the membrane. MPPA could already be detected in the extracting solution after less than 1 hr of membrane extraction and showed a continuous increase over time. In contrast, IPA could only be found in the acidic extracting solution after about 7 h of membrane extraction.

Again, these results indicate that the uncharged/charged ratio of the amine at the pH of the feed solution is not the main driving force for the membrane separation, as this is similar for both amines. Rather, these results indicate that the hydrophobic character of the amine (as e.g. expressed by the log P value) determines the membrane separation behaviour. Again, no water transport over the membrane was observed.

Example 3

An enzymatically catalysed transamination reaction is performed in an organic solvent, using benzyl acetone (BA) and isopropyl amine (IPA) as respectively substrate ketone and substrate amine. This setup is chosen in view of the limited solubility of BA in aqueous liquids (10 mM or 1.48 g/l). The resulting products are acetone (as co-product ketone) and (S-)1-methyl-3-phenylpropylamine (S-MPPA—a chiral amine). This reaction is prone to product inhibition by MPPA.

The reaction mixture is passed through a membrane contactor module, using an acidic sodium acetate buffer (pH 3) as extracting solution. In line with example 2, the MPPA product efficiently passes the membrane and MPPA can be obtained with a high yield, while the amine donor IPA mainly remains in the feed solution.

What is claimed is:

1. A method for a separation of an amine or an organic acid from a first solution comprising at least one amine or at least one organic acid, comprising:
    (i) contacting said first solution comprising at least one amine or at least one organic acid with a non-liquid hydrophobic membrane; and
    (ii) extracting the amine or the organic acid, from said first solution comprising at least one amine or at least one organic acid into a second solution across said non-liquid hydrophobic membrane, wherein said non-liquid hydrophobic membrane separates said first solution and said second solution, and wherein said non-liquid hydrophobic membrane is a porous inorganic membrane functionalized with an organic functional group.

2. The method according to claim 1, wherein said porous inorganic membrane comprises an oxide or hydroxide of an element M1, and wherein said organic functional group is linked to said inorganic membrane via a M1-carbon bond, a M1-O—P-carbon bond or a M1-O—Si-carbon bond.

3. The method according to claim 1, wherein said organic functional group is selected from the group consisting of (a) haloalkyl, preferably fluoroalkyl or perfluoroalkyl, more preferably fluoro$C_1$-$C_{16}$alkyl or perfluoro$C_1$-$C_{16}$alkyl, more preferably fluoro$C_1$-$C_8$alkyl or (per)fluoro$C_1$-$C_8$alkyl; (b) aryl, preferably $C_6$-$C_{16}$aryl, more preferably $C_6$-$C_{10}$aryl; and (c) haloaryl, preferably fluoroaryl or perfluoroaryl, more preferably fluoro$C_6$-$C_{16}$aryl or perfluoro$C_6$-$C_{16}$aryl, more preferably fluoro$C_6$-$C_{10}$aryl or perfluoro$C_6$-$C_{10}$aryl.

4. The method according to claim 1, wherein said second solution is an aqueous solution, and wherein a pH value of said second solution is adapted so that said amine or said organic acid extracted across said non-liquid hydrophobic membrane is essentially in its charged state to prevent a back extraction of said amine or said organic acid across said non-liquid hydrophobic membrane.

5. The method according to claim 4, wherein
    (a) said aqueous solution of the second solution has a pH at least 2 or at least 3 units below a pKa value of the amine which has been extracted from the first solution to obtain said amine in its dissociated (charged) form; or
    (b) said aqueous solution of the second solution has a pH at least 2 or at least 3 units above a pKa value of the organic acid, which has been extracted from the first solution to obtain the organic acid in its dissociated (charged) form.

6. The method according to claim 1, wherein said first solution is an aqueous solution, preferably with a pH value differing from a pKa value of the amine or organic acid by about 2.0 units or less, preferably by 1.0 unit or less.

7. The method according to claim 1, further comprising:
    (iii) recovering the amine or organic acid extracted across said non-liquid hydrophobic membrane in said step (ii) from said second solution.

8. The method according to claim 1, wherein said first solution comprises at least one first amine and at least one second amine, with the first and second amine differing in hydrophobicity, expressed as a difference in Log P value, and wherein in said step (ii) the amine with the highest Log P value is extracted from said first solution across said non-liquid hydrophobic membrane.

9. The method according to claim 1, wherein said first solution comprises at least one chiral amine.

10. The method according to claim 9, further comprising:
    Forming the chiral amine by contacting an amino donor and a prochiral amino acceptor with a transaminase to obtain the chiral amine in said first solution prior to said steps (i) and (ii).

11. The method according to claim 10, wherein the amino donor is 2-propyl amine.

12. The method according to claim 9, wherein said first solution is an aqueous alkaline solution.

13. The method according to claim 9, wherein said first solution is an organic solvent solution.

14. The method according to claim 1, wherein the first solution is fed to a first compartment of a membrane contactor module, and wherein said step (ii) transfers said organic amine to a second compartment of the membrane contactor module comprising said second solution.

15. The method according to claim 1, wherein the porous inorganic membrane has a pore size ranging from about 0.5 nm to about 100 nm.

16. The method according to claim 2, wherein the element M1 is a metal or silicon.

* * * * *